(12) United States Patent
Mehta et al.

(10) Patent No.: US 8,744,872 B1
(45) Date of Patent: Jun. 3, 2014

(54) SYSTEM AND METHOD FOR PHARMACOVIGILANCE

(71) Applicants: Rajesh Revachand Mehta, New York, NY (US); Henry George Wei, New York, NY (US); Gregory Brian Steinberg, Dingmans Ferry, PA (US)

(72) Inventors: Rajesh Revachand Mehta, New York, NY (US); Henry George Wei, New York, NY (US); Gregory Brian Steinberg, Dingmans Ferry, PA (US)

(73) Assignee: Aetna, Inc., Hartford, CT (US)

( * ) Notice: Subject to any disclaimer, the term of this patent is extended or adjusted under 35 U.S.C. 154(b) by 0 days.

(21) Appl. No.: 13/733,791

(22) Filed: Jan. 3, 2013

(51) Int. Cl.
*G06F 19/00* (2011.01)

(52) U.S. Cl.
CPC ................................. *G06F 19/3443* (2013.01)
USPC ............................................................ 705/2

(58) Field of Classification Search
USPC ........................................ 705/2, 3; 345/440
See application file for complete search history.

(56) References Cited

U.S. PATENT DOCUMENTS

| | | | | |
|---|---|---|---|---|
| 2003/0046110 | A1* | 3/2003 | Gogolak | 705/2 |
| 2007/0294112 | A1* | 12/2007 | Settimi | 705/3 |
| 2010/0223068 | A1* | 9/2010 | Von Schweber et al. | 705/2 |
| 2013/0016106 | A1* | 1/2013 | Yip et al. | 345/440 |

OTHER PUBLICATIONS

"The Sentinel Initiative—National Strategy for Monitoring medical Product Safety"; May 2008; FDA.*

* cited by examiner

*Primary Examiner* — John Pauls
(74) *Attorney, Agent, or Firm* — Leydig, Voit & Mayer, Ltd.

(57) ABSTRACT

A method, computer-readable storage medium, and system for analyzing a relationship between one or more agents and one or more clinical outcomes. The method includes: receiving a selection of one or more agents; receiving a selection of one or more clinical outcomes; for each of the one or more agents, analyzing clinical data stored in a database to determine a number of occurrences of each of the one or more clinical outcomes when the agent is administered; for each of the one or more agents, calculating a risk score for each clinical outcome corresponding to the number of occurrences of the clinical outcome; and outputting the risk scores to a graphical display.

22 Claims, 10 Drawing Sheets

SYSTEM AND METHOD FOR PHARMACOVIGILANCE

FIELD

This disclosure relates generally to the field of health care management and, more specifically, to a system and method for pharmacovigilance.

BACKGROUND

Pharmacovigilance is the science of collecting, monitoring, researching, assessing, and evaluating information from healthcare providers and patients on the adverse effects of medications with a view towards identifying hazards associated with the medications and preventing harm to patients.

A typical health care system includes a variety of participants, including doctors, hospitals, insurance carriers, and patients, among others. These participants frequently rely on each other for the information necessary to perform their respective roles because individual care is delivered and paid for in numerous locations by individuals and organizations that are typically unrelated. As a result, a plethora of health care information storage and retrieval systems are required to support the heavy flow of information between these participants related to patient care. Critical patient data is stored across many different locations using legacy mainframe and client-server systems that may be incompatible and/or may store information in non-standardized formats. To ensure proper patient diagnosis and treatment, health care providers often request patient information by phone or fax from hospitals, laboratories, or other providers. Therefore, disparate systems and information delivery procedures maintained by a number of independent health care system constituents lead to gaps in timely delivery of critical information and compromise the overall quality of clinical care. Since a typical health care practice is concentrated within a given specialty, an average patient may be using services of a number of different specialists, each potentially having only a partial view of the patient's medical status.

Moreover, pharmacovigilance is facing increased pressure from regulators and academics who are mining real-world databases for safety signals. Some factors affecting the pharmacovigilance landscape include: an increasing use of real-world data by regulators; heightened expectations of manufacturers from the FDA (Food and Drug Administration), public, and academics/investigators; externalization of safety data (e.g., EMR (electronic medical records); and emergence of pharmacovigilance as an applied science.

There are certain limitations to the way in which pharmacovigilance is currently being implemented. Firstly, pharmacovigilance, or drug surveillance, is typically done by "ad hoc" reporting, where a physician independently identifies patients that have a problem with a certain drug and report this singular instance to the FDA. The FDA then accumulates this information and communicates with pharmaceutical manufacturers. This process is inefficient and ineffective. To overcome some of the drawbacks of the ad hoc approach, the FDA has implemented the "Sentinel" and "Mini Sentinel" initiatives. However, these initiatives look at retrospective and/or historical data to perform drug surveillance.

Accordingly, there remains a need in the art for a system and method for pharmacovigilance that overcomes the drawbacks and limitations of current approaches.

SUMMARY

Some embodiments of the disclosure provide a method, computer-readable storage medium, and system for analyzing a relationship between one or more agents and one or more clinical outcomes. The method includes: receiving a selection of one or more agents; receiving a selection of one or more clinical outcomes; for each of the one or more agents, analyzing clinical data stored in a database to determine a number of occurrences of each of the one or more clinical outcomes when the agent is administered; for each of the one or more agents, calculating a risk score for each clinical outcome corresponding to the number of occurrences of the clinical outcome; and outputting the risk scores to a graphical display.

DETAILED DESCRIPTION

Embodiments of the disclosure provide a system and method for pharmacovigilance. According to some embodiments, health related clinical data is stored in one or more databases. The clinical data may include, for each patient, demographic data, diagnostic codes, procedure codes, medication and prescription data, and lab data, among others. Clinical data may include also data from electronic medical records (EMRs). A processor is configured to receive a selection of one or more agents (e.g., drugs) and one or more clinical outcomes (e.g., adverse events). The processor is configured to calculate a risk score for the one or more clinical outcomes in relation to the one or more agents. According to various embodiments, the risk score may be an absolute risk or a relative risk. A chi-squared statistical analysis and a p-value statistical analysis may also be performed to confirm or reject the observed calculations.

Accordingly, some embodiments provide a proactive, prospective, and ongoing approach to pharmacovigilance. The database from which the analysis is performed is continuously being updated with new clinical data. For example, medical claims data may be entered into the database within 48 hours of an insurance carrier receiving information about the treatment.

Some embodiments disclosed herein provide a proactive and automated signal detection and surveillance system with standardized reporting. Some embodiments provide real-time monitoring due to rapid adjudication and incorporation of claims data into analytic database, and a signal validation system that can exonerate or stratify risk in near real-time and identify potential benefits, versus an industry average of six to nine months.

Figure 1:
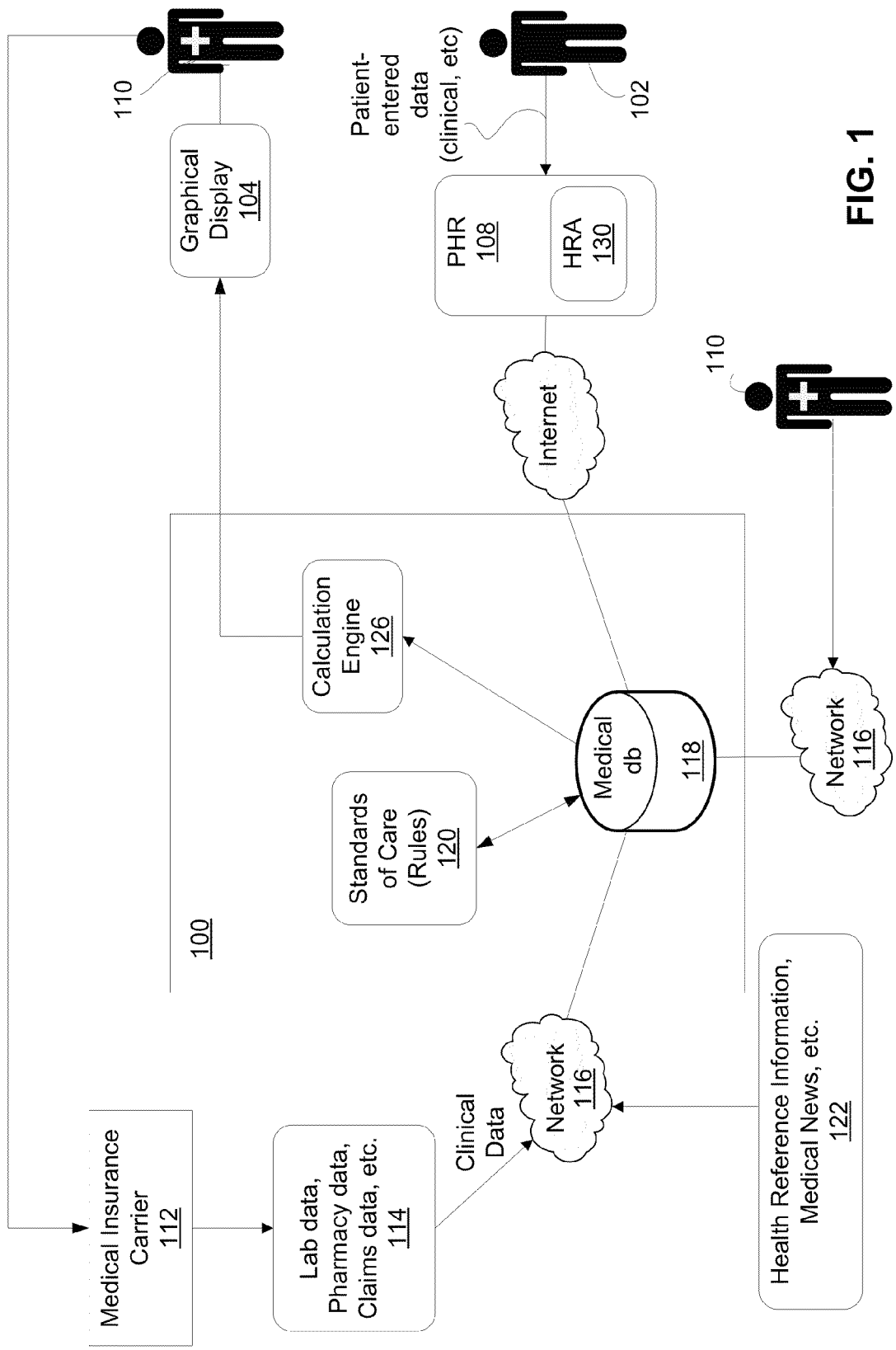
FIG. 1 is a schematic diagram illustrating an overview of a system for analyzing a relationship between one or more agents and one or more clinical outcomes, in accordance with an embodiment of the disclosure.

Turning to the figures, FIG. 1 is a schematic diagram illustrating an overview of a system for analyzing a relationship between one or more agents and one or more clinical outcomes, in accordance with an embodiment of the disclosure. A health care organization 100 collects and processes a wide spectrum of medical care information relating to a patient 102 in order to analyze the relationship between one or more agents and one or more clinical outcomes. A personal health record (PHR) 108 of a patient 102 may be configured to solicit the patient's input for entering additional pertinent medical information, tracking follow-up actions, and allowing the health care organization 100 to track the patient's medical history.

When the patient 102 utilizes the services of one or more health care providers 110, a medical insurance carrier 112 collects the associated clinical data 114 in order to administer the health insurance coverage for the patient 102. Additionally, a health care provider 110, such as a physician or nurse, enters clinical data 114 into one or more health care provider applications pursuant to a patient-health care provider interaction during an office visit or a disease management interaction. Clinical data 114 originates from medical services claims, pharmacy data, as well as from lab results, and includes information associated with the patient-health care provider interaction, including information related to the patient's diagnosis and treatment, medical procedures, drug prescription information, in-patient information, and health care provider notes, among other things. The medical insurance carrier 112 and the health care provider 110, in turn, provide the clinical data 114 to the health care organization 100, via one or more networks 116, for storage in one or more medical databases 118. The medical databases 118 are administered by one or more server-based computers associated with the health care provider 100 and comprise one or more medical data files located on a computer-readable medium, such as a hard disk drive, a CD-ROM, a tape drive, or the like. The medical databases 118 may include a commercially available database software application capable of interfacing with other applications, running on the same or different server based computer, via a structured query language (SQL). In an embodiment, the network 116 is a dedicated medical records network. Alternatively, or in addition, the network 116 includes an Internet connection that comprises all or part of the network.

In some embodiments, an on-staff team of medical professionals within the health care organization 100 consults various sources of health reference information 122, including evidence-based preventive health data, to establish and continuously or periodically revise a set of clinical rules 120 that reflect best evidence-based medical standards of care for a plurality of conditions. The clinical rules 120 are stored in the medical database 118.

To supplement the clinical data 114 received from the insurance carrier 112, the PHR 108 allows patient entry of additional pertinent medical information that is likely to be within the realm of patient's knowledge. Examples of patient-entered data include additional clinical data, such as patient's family history, use of non-prescription drugs, known allergies, unreported and/or untreated conditions (e.g., chronic low back pain, migraines, etc.), as well as results of self-administered medical tests (e.g., periodic blood pressure and/or blood sugar readings). Preferably, the PHR 108 facilitates the patient's task of creating a complete health record by automatically populating the data fields corresponding to the information derived from the medical claims, pharmacy data and lab result-based clinical data 114. In one embodiment, patient-entered data also includes non-clinical data, such as upcoming doctor's appointments. In some embodiments, the PHR 108 gathers at least some of the patient-entered data via a health risk assessment tool (HRA) 130 that requests information regarding lifestyle, behaviors, family history, known chronic conditions (e.g., chronic back pain, migraines, etc.), and other medical data, to flag individuals at risk for one or more predetermined medical conditions (e.g., cancer, heart disease, diabetes, risk of stroke, etc.) pursuant to the processing by a calculation engine 126. Preferably, the HRA 130 presents the patient 102 with questions that are relevant to his or her medical history and currently presented conditions. The risk assessment logic branches dynamically to relevant and/or critical questions, thereby saving the patient time and providing targeted results. The data entered by the patient 102 into the HRA 130 also populates the corresponding data fields within other areas of PHR 108. The health care organization 100 aggregates the clinical data 114 and the patient-entered data, as well as the health reference and medical news information 122, into the medical database 118 for subsequent processing via the calculation engine 126.

The health care organization 100 includes a multi-dimensional analytical software application including a calculation engine 126 comprising computer-readable instructions for performing statistical analysis on the contents of the medical databases 118 in order to analyze a relationship between one or more agents and one or more clinical outcomes. The relationships identified by the calculation engine 126 can be presented in a graphical display 104, e.g., to the healthcare provider 110 and/or medical insurance carrier 112 and/or to the government (e.g., FDA).

After collecting the relevant data, the calculation engine 126 receives a selection of one or more agents. In one example implementation, the agents are prescription drugs. The calculation engine calculates a risk of occurrence of one or more clinical outcomes for each of the one or more agents. In one implementation, a drug may be exonerated from causing a clinical outcome that is detected, for example, in spontaneous reports or for specific subgroups (or possibly overall). In another example implementation, the calculation engine 126 may determine that certain adverse events occur mostly in off-label use. "Off-label" use refers to non-recommended uses of a drug, such as non-FDA approved uses. In another implementation, calculation engine 126 may determine how a drug's safety profile compares to other drugs within the same class of drugs. Other use cases are also within the scope of embodiments of the disclosure, as described in greater detail herein.

For example, embodiments disclosed herein can provide "comparative effectiveness" information by directly comparing multiple pharmacologically similar agents against varied and multiple health outcomes of interest, allowing for inferences to be made about the comparative risks and benefits of these agents. This analysis may lead to the identification of new therapeutic indications for existing agents.

While the entity relationships described above are representative, those skilled in the art will realize that alternate arrangements are possible. In one embodiment, for example, the health care organization 100 and the medical insurance carrier 112 is the same entity. Alternatively, the health care organization 100 is an independent service provider engaged in collecting, aggregating, and processing medical care data from a plurality of sources to provide a personal health record (PHR) service for one or more medical insurance carriers 112. In yet another embodiment, the health care organization 100 provides PHR services to one or more employers by collecting data from one or more medical insurance carriers 112.

Figure 2:
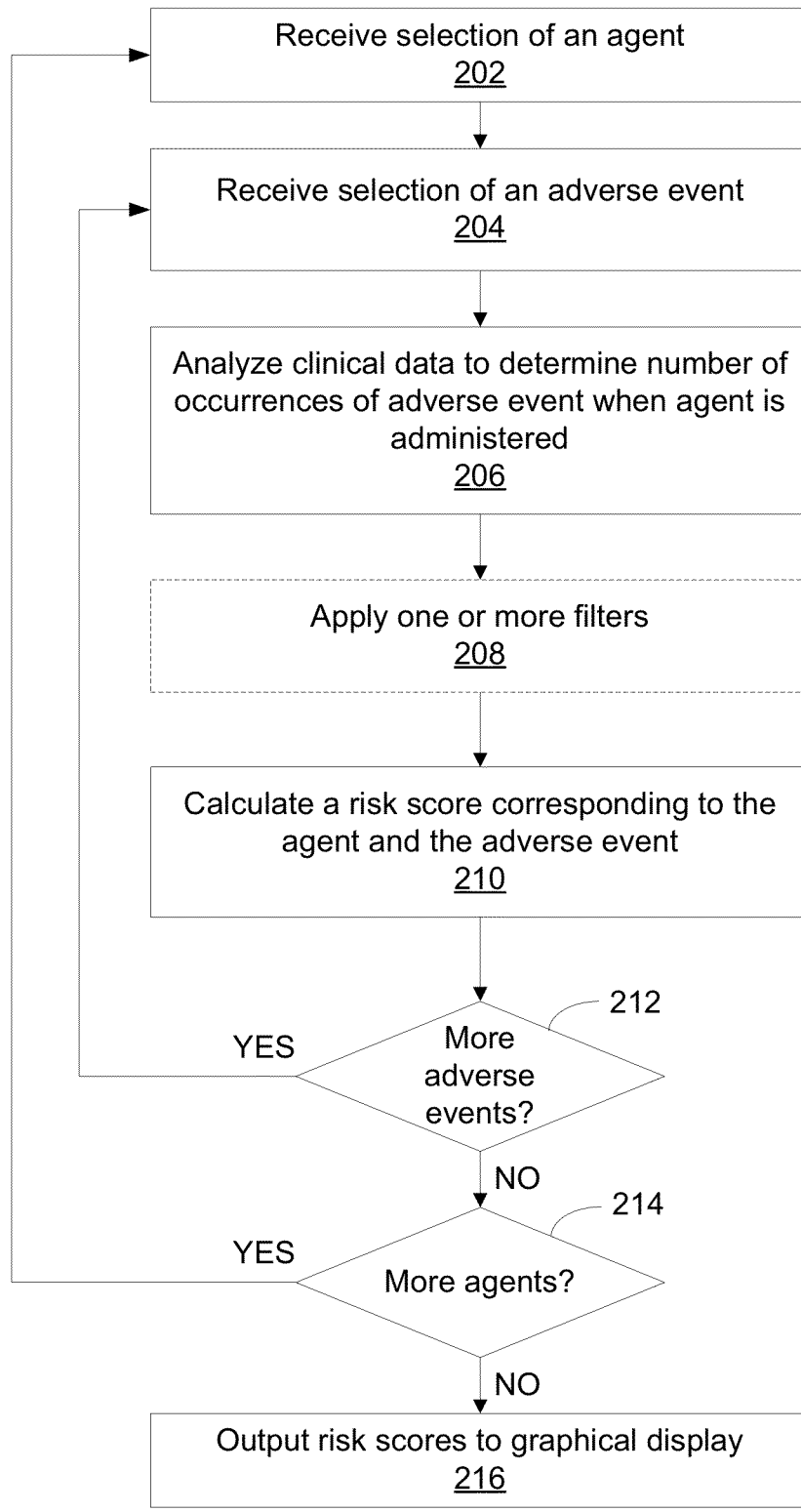
FIG. 2 is a flow diagram illustrating a method for analyzing a relationship between one or more agents and one or more clinical outcomes, in accordance with an embodiment of the disclosure.

FIG. 2 is a flow diagram illustrating a method 200 for analyzing a relationship between one or more agents and one or more clinical outcomes, in accordance with an embodiment of the disclosure. As shown, the method 200 begins at step 202, where a processor, such as a processor associated with the calculation engine 126, receives a selection of an agent. In one embodiment, the agent is a prescription drug. At step 204, the processor receives selection of an adverse event. In some embodiments, adverse events are clinic events. Non-limiting examples include accidents, cancer, congestive heart failure, depression, diarrhea, glaucoma, infection, liver dysfunction, lymphoma, major bleeding, renal failure, seizures, sudden death, suicide, among many others. In some embodiments, the adverse events are coded according to standard external definitions (for example, by the government). In other embodiments, the adverse events are coded according to proprietary definitions.

At step 206, the processor analyzes clinical data in a database to determine a number of occurrences of the adverse event when the agent is administered. As described, the clinical data can come from many sources, including demographic data, claims data, procedure codes, diagnostic codes, pharmacy/prescription data, patient-entered data, among others. The processor analyzes the data to identify a number of patients that have exhibited the adverse event when taking the drug for a predetermined minimum amount of time (for example, 6 months).

At step 208, the processor applies one or more filters. The clinical data can be filtered according to certain parameters, such as patient age, gender, demographic info, clinical stratification scores and identified conditions, and whether the use of the drug was "on-label" or "off-label" (i.e., "on-label" refers to use in the recommended or FDA approved manner; "off-label" refers to use in a non-recommended or non-FDA approved manner), among others. The analysis performed at step 206 can, therefore, be applied only to the data that satisfies the filters. In some embodiments, step 208 is performed before step 206. Also, in some embodiments, step 208 is optional and is omitted. In such a case, no filter is applied, and all the clinical data is analyzed.

At step 210, the processor calculates a risk score corresponding to the adverse event and the agent. According to some embodiments, the risk score can be an absolute risk or a relative risk. Table 1 below illustrates occurrences of the adverse event when a particular drug is administered, a total number of patients that suffered the adverse event, a total number of patients to whom the drug was administered, and a total number of patients to whom the drug was not administered.

TABLE 1

|  | Drug | No Drug | Total |
|---|---|---|---|
| Adverse Event | IAO |  | IO |
| No Adverse Event |  |  |  |
| Total | IA |  | I |

In Table 1, "IAO" refers to the occurrence of the adverse event when the drug is administered, "IO" refers to the total number of patients that suffered the adverse event, "IA" refers to the total number of patients to whom the drug was administered, and "I" refers to the total number of patients.

According to one embodiment, an "ON agent risk," "NO agent risk," "Absolute Risk," and "Relative Risk" can be calculated using Equations 1 to 4, respectively:

$$ONagentRisk = \frac{IAO}{IA}, \quad \text{(Equation 1)}$$

$$NOagentRisk = \frac{IO - IAO}{I - IA}, \quad \text{(Equation 2)}$$

$$AbsoluteRisk = ONagentRisk - NOagentRisk, \quad \text{(Equation 3)}$$

and $$RelativeRisk = \frac{ONagentRisk}{NOagentRisk}. \quad \text{(Equation 4)}$$

A "chi-squared" analysis can also be performed to calculate a confidence level for the statistical analysis performed using Equation 5:

$$\chi^2 = \frac{(I)[(IAO)(I - IO - IA + IAO) - (IO - IAO)(IA - IAO)]^2}{(IA)(I - IA)(IO)(I - IO)}. \quad \text{(Equation 5)}$$

In some embodiments, a "P-value" may be calculated to test the statistical significance of the calculations.

Table 2, below, illustrates an example where the adverse event is congestive heart failure (CHF) and the drug is an ACE inhibitor.

TABLE 2

|  | Drug | No Drug | Total |
|---|---|---|---|
| Adverse Event | 568 |  | 2433 |
| No Adverse Event |  |  |  |
| Total | 179499 |  | 656938 |

As shown, a total of 179499 patients took the drug and 568 experienced the adverse effect. A total of 2433 patients experienced the adverse effect. A total of 656938 patients did not take the drug.

Using the Equations 1-4 above, the relative risk is calculated at 0.81. The chi-squared value is calculated using Equation 5 as 19.49.

At step 212, the processor determines whether there are more adverse events to analyze for the selected agent/drug. If the processor determines that there are more adverse events to analyze for the selected agent/drug, then the method 200 returns to step 204, described above. If the processor determines that there are no more adverse events to analyze for the selected agent/drug, then the method 200 proceeds to step 214.

At step 214, the processor determines whether there are more agents/drugs to analyze against adverse events. If the processor determines that there are more agents/drugs to analyze, then the method 200 returns to step 202, described above. If the processor determines that there are no more agents/drugs to analyze, then the method 200 proceeds to step 216.

At step 216, the processor outputs results (i.e., risk scores) to a graphical display. In some embodiments, the results may be graphically represented as a "heat map," where a circle corresponds to the average relative risk of the drug-adverse event combination, and where a greater size of the circle corresponds to a greater average relative risk. Examples are provided below in FIGS. 3-9.

Figure 3:
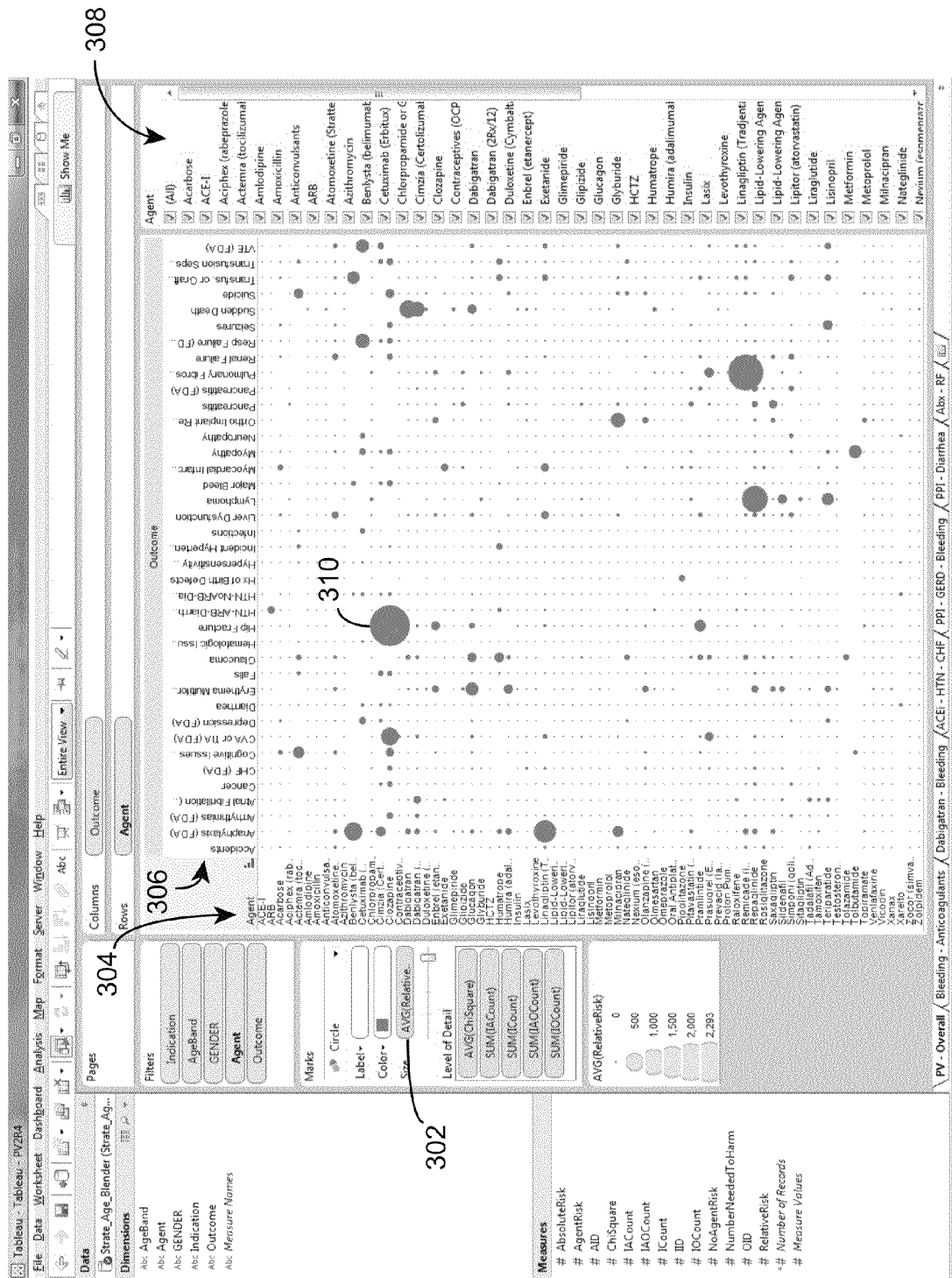
FIG. 3 is a screenshot of a user interface displaying an average relative risk for plurality of agents versus a plurality of outcomes, in accordance with an embodiment of the disclosure.

FIG. 3 is a screenshot of a user interface displaying an average relative risk for plurality of agents versus a plurality of outcomes, in accordance with an embodiment of the disclosure. As shown, a listing of different agents (for example, prescription drugs) is shown along a vertical axis 304 and a listing of different outcomes (for example, adverse clinical events) is shown along a horizontal axis 306. A selection of which agents and/or outcomes are shown in the user interface can be made via interface element 308 via one or more checkboxes. Note, in FIG. 3, the selection of different outcomes is not shown (i.e., a user would need to "scroll down" to see the checkboxes for the different outcomes).

As described above, a processor can calculate a risk score, such as average relative risk, for each combination of agent and outcome. In the example shown in FIG. 3, average relative risk is graphically displayed such that an increase in the size 302 of the circle shown for the particular agent-outcome combination corresponds to an increase in the average relative risk. For example, a high average relative risk is exhibited between the agent "Clozapine" and the outcome "Hip fracture," displayed as circle 310.

Figure 4:
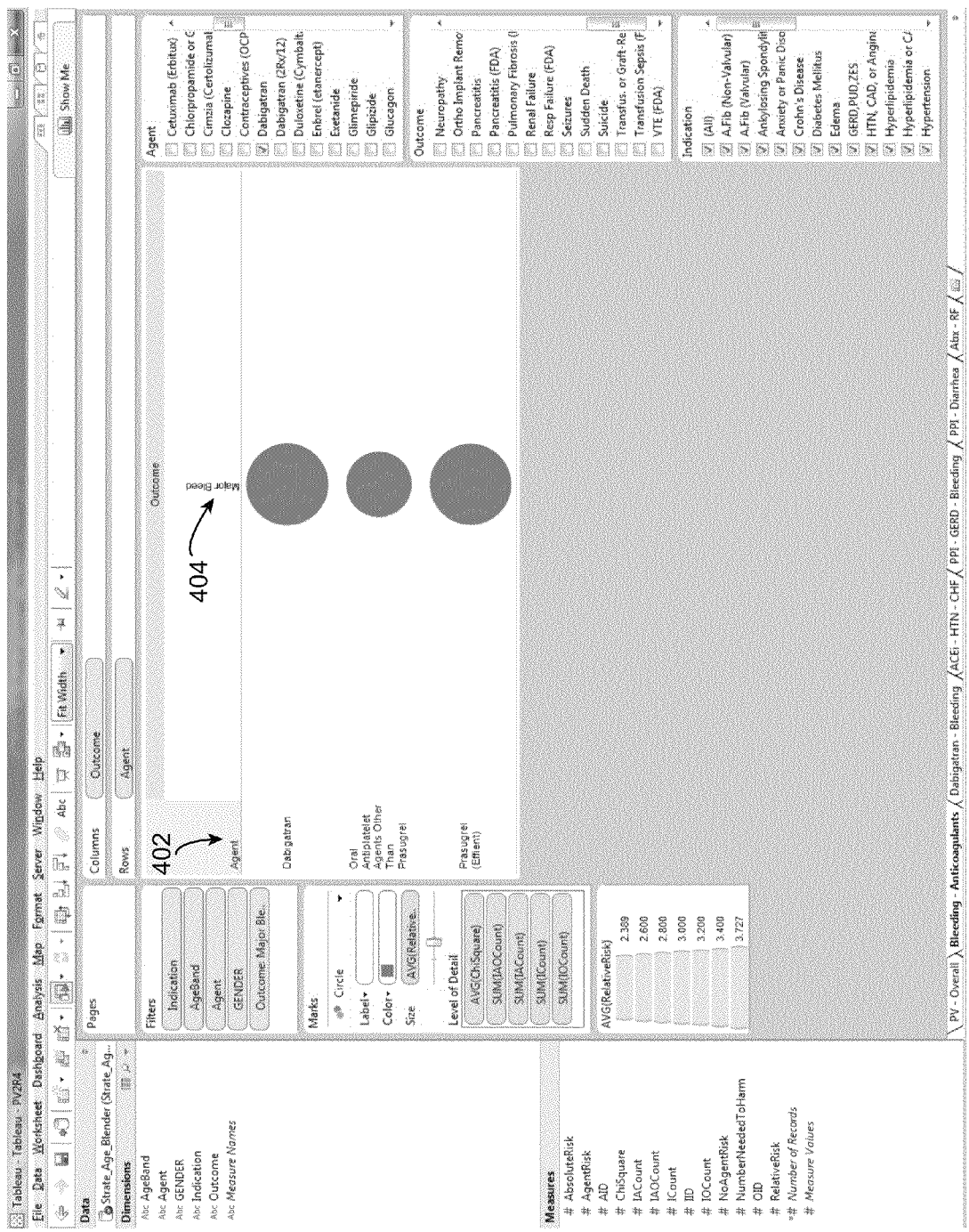
FIG. 4 is a screenshot of a user interface displaying an average relative risk for different agents in the same class of agents relative to a particular outcome, in accordance with an embodiment of the disclosure.

FIG. 4 is a screenshot of a user interface displaying an average relative risk for different agents in the same class of agents relative to a particular outcome, in accordance with an embodiment of the disclosure. In the example shown in FIG. 4, three different blood thinners are shown along a vertical axis 402 relative to a particular outcome (e.g., major bleeding) along a horizontal axis 404. In the example shown, the three blood thinners are "Dabigatran," "Prasugrel," and "oral antiplatelet agents other than Prasugrel." With respect the particular outcome shown, it is readily apparent from the sizes of the circles, that the agent "oral antiplatelet agents other than Prasugrel" has the lowest average relative risk of the three agents. Providing a graphical representation of the average relative risk provides for a superior user experience, when compared to conventional techniques.

Figure 5:
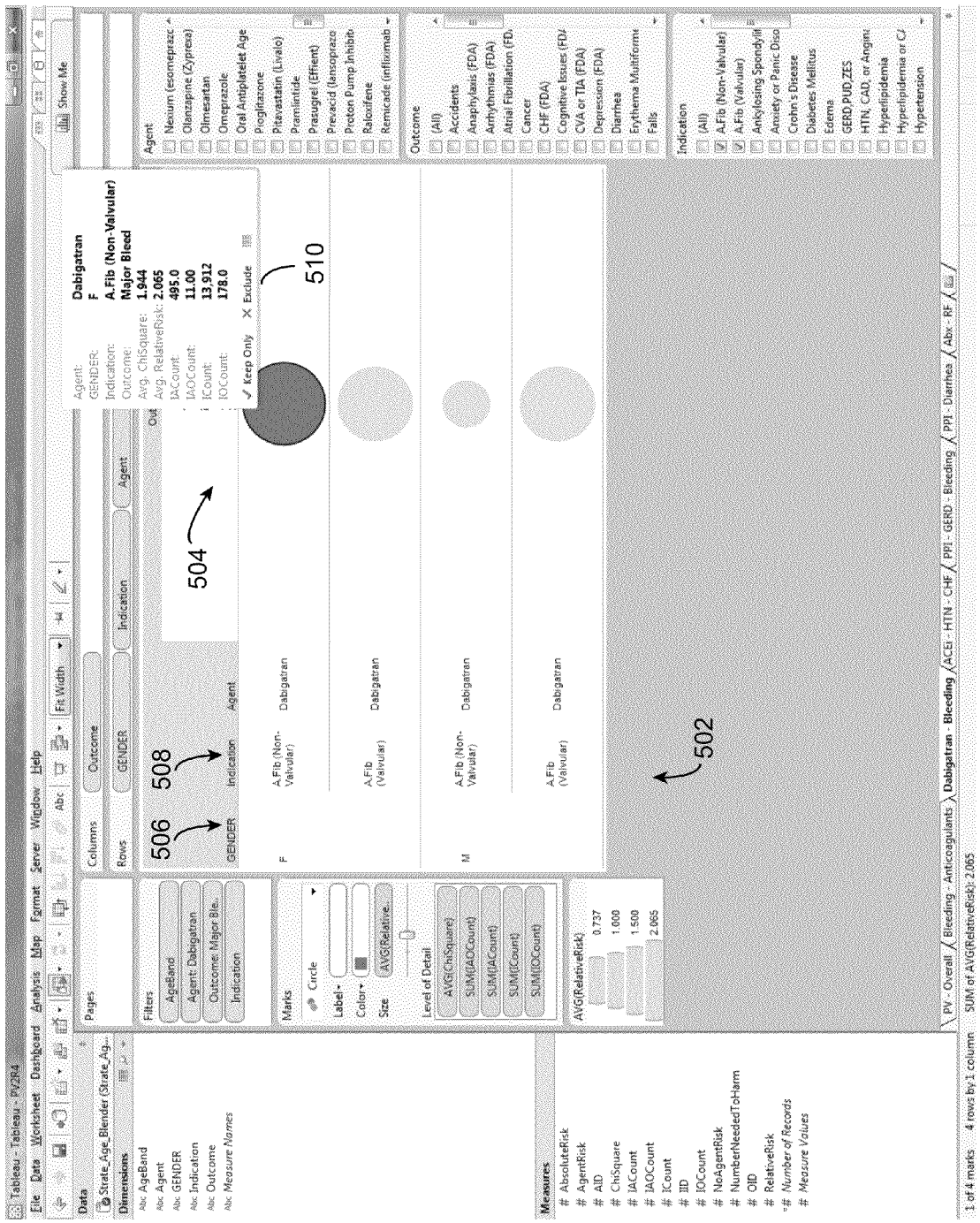
FIG. 5 is a screenshot of a user interface displaying an average relative risk for one agent relative to one outcome, where the data is sorted by one or more filters, in accordance with an embodiment of the disclosure.

FIG. 5 is a screenshot of a user interface displaying an average relative risk for one agent relative to one outcome, where the data is sorted by one or more filters, in accordance with an embodiment of the disclosure. As described, the data can be filtered using one or more filters prior to performing the statistical analysis. In the example shown in FIG. 5, a single outcome (e.g., major bleeding) is shown along a horizontal axis 504. Along the vertical axis 502, a single agent is shown (e.g., "Dabigatran"), where the data is first filtered by gender 506 and then by indication 508. Filtering by "indication," in this example, refers to whether the drug was used in an FDA approved manner (i.e., "on-label") or a non-FDA approved manner (i.e., "off-label"). In the example in FIG. 5, A.Fib "Non-Valvular" refers to the FDA approved mode of administering Dabigatran, and A.Fib "Valvular" refers to the non-FDA approved mode of administering Dabigatran. When comparing the average relative risk for the four different combinations of gender 506 and indication 508, the outcome has a similar average relative risk for both indications (i.e., Non-Valvular and Valvular) for females. However, for males, the Valvular (i.e., non-FDA approved) mode of administering the drug has a significantly greater average relative risk. The outcome shown in FIG. 5 may suggest that a blanket statement from the FDA that prohibits Valvular treatment with Dabigatran (for both males and females) is not necessary, and that the FDA should consider allowing Valvular treatments for women. The results shown using embodiments of the disclosure are not meant to be definitive proof that certain drugs do not cause certain complications/outcomes, but rather to generate a hypothesis for further investigation and/or research.

In addition, in some embodiments, a user can click on or hover a cursor over one of the circles, which causes a dialog box 510 to be displayed. The dialog box 510 includes various counts and statistics for the particular agent-outcome pair.

Figure 6:
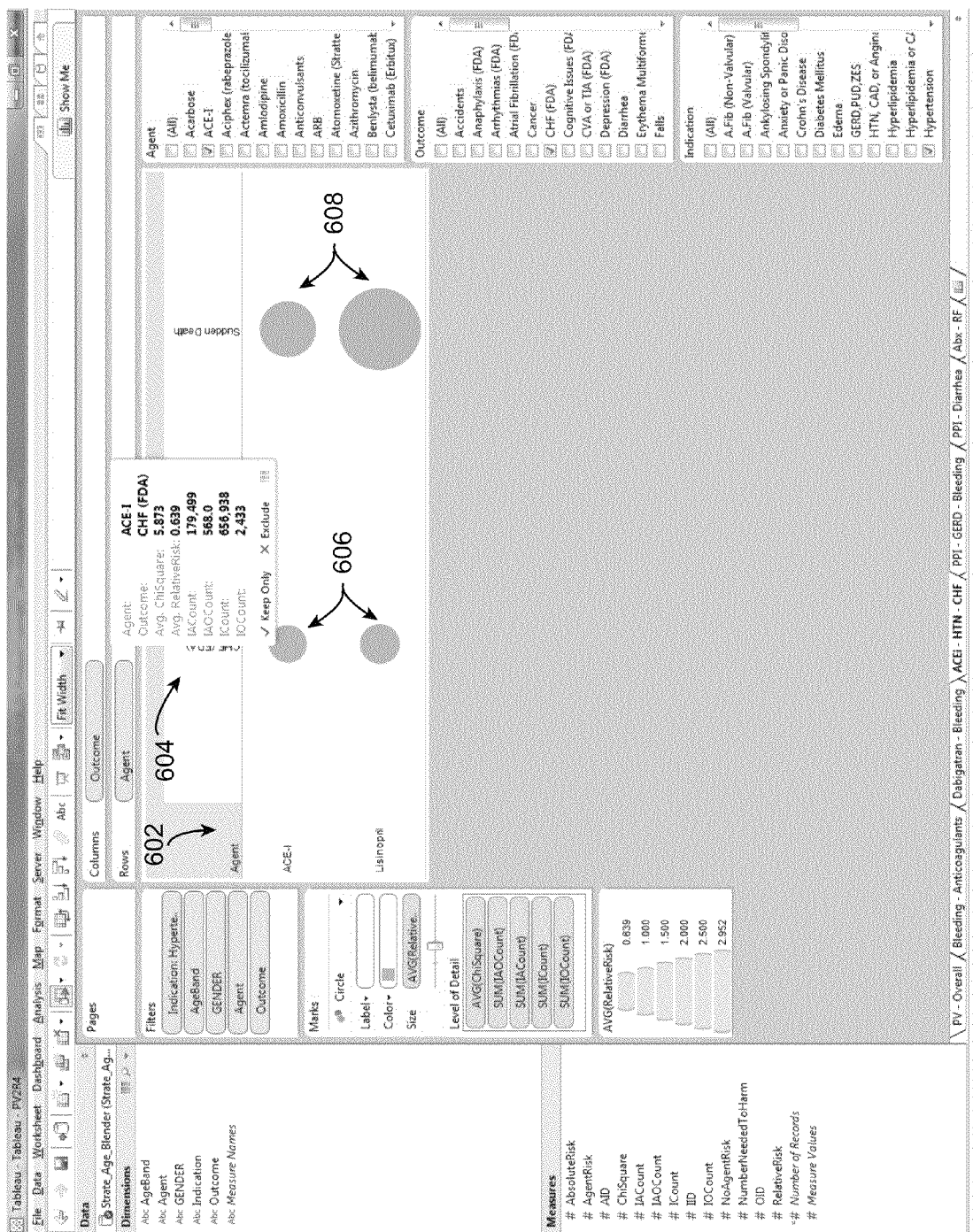
FIGS. 6-8 are screenshots of user interfaces displaying an average relative risk for a plurality of outcomes for one agent relative to other agents in the same class of agents, in accordance with several embodiments of the disclosure.
Figure 7:
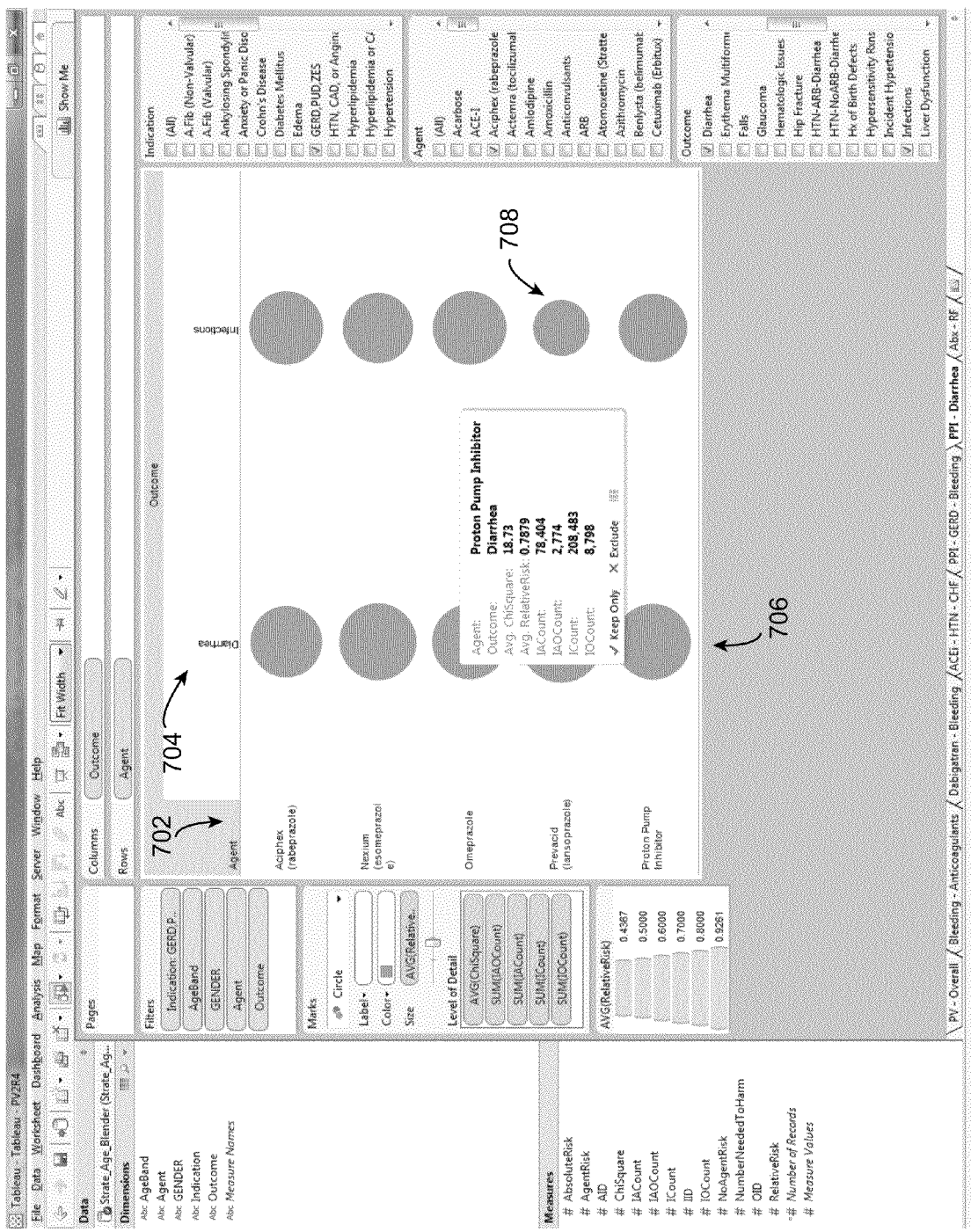
Figure 8:
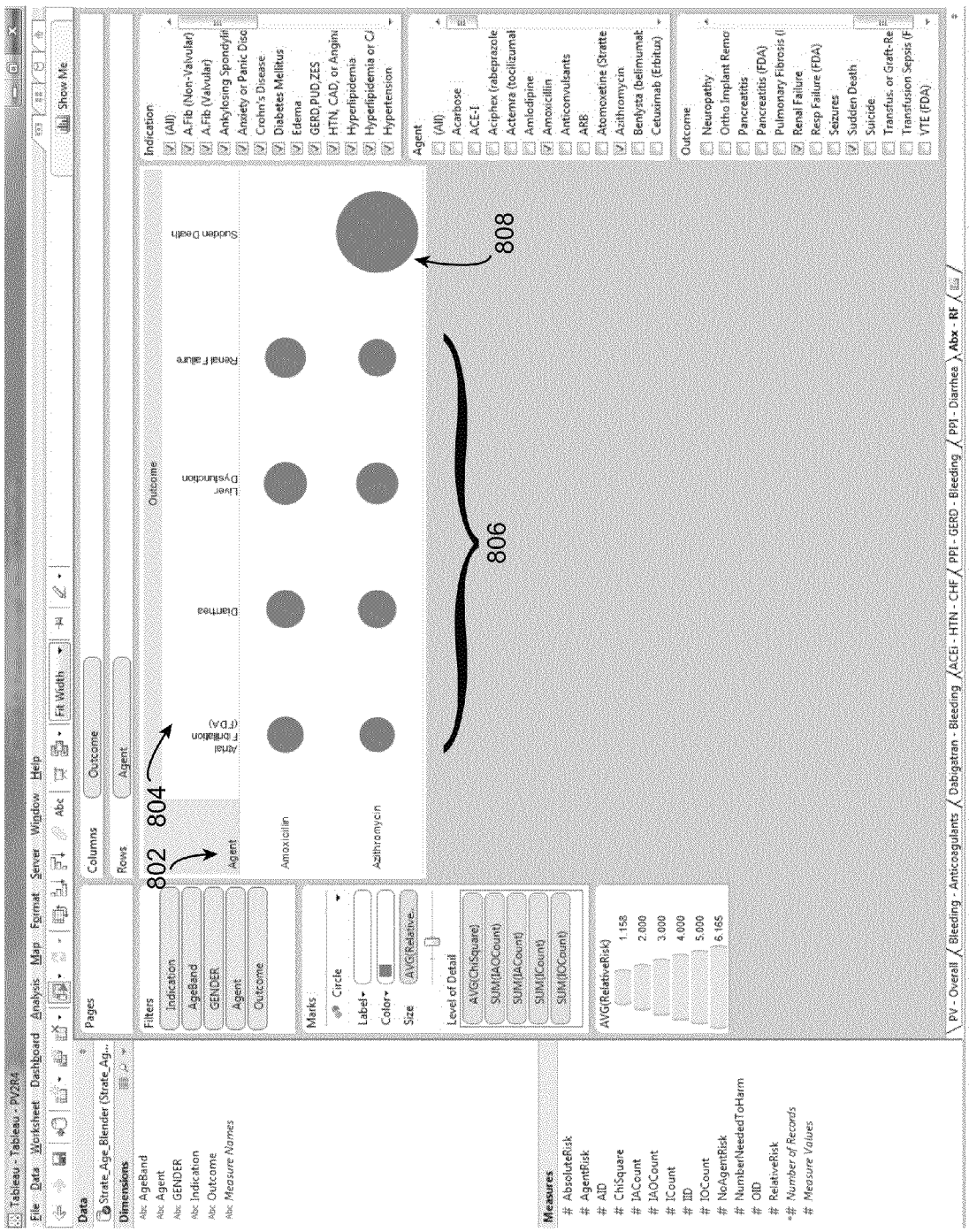

FIGS. 6-8 are screenshots of user interfaces displaying an average relative risk for a plurality of outcomes for one agent relative to other agents in the same class of agents, in accordance with several embodiments of the disclosure.

In FIG. 6, two different outcomes are shown along the horizontal axis 604 (i.e., CHF (congestive heart failure) and sudden death). Along the vertical axis 602, a single agent is shown (i.e., "Lisinopril," an ACE inhibitor) along with an agent grouping (i.e., "ACE-I"), which corresponds to all ACE inhibitors, including the single agent shown separately. As shown in the example in FIG. 6 via circles 606, Lisinopril has a similar average relative risk for CHF as all ACE inhibitors. However, as shown via circles 608, Lisinopril has a higher average relative risk for sudden death compared to all ACE inhibitors. This finding could cause physicians and/or the FDA to place certain warnings on Lisinopril.

In FIG. 7, two different outcomes are shown along the horizontal axis 704 (i.e., diarrhea and infections). Along the vertical axis 702, five different agents from the same class are shown. In this example, five different proton pump inhibitors are shown. As shown in the example in FIG. 7 via circles 706, each of the five proton pump inhibitors has a similar average relative risk for diarrhea. However, with respect to infections, "Prevacid" has a lower average relative risk as compared to the other four proton pump inhibitors, as evidenced by the smaller size of circle 708. As such, in one example, this information tends to show that Prevacid may be superior to the other proton pump inhibitors since the risk for diarrhea is roughly the same as for the other proton pump inhibitors, but with a lower risk for infections.

In FIG. 8, five different outcomes are shown along the horizontal axis 804. Along the vertical axis 802, two different agents from the same class are shown. In this example, two different antibiotics are shown, amoxicillin and azithromycin. As shown in the example in FIG. 8 via circles 806, both antibiotics have similar average relative risk for four of the five outcomes shown. However, with respect to the outcome "sudden death," azithromycin has a relatively large average relative risk (as shown via circle 808) and amoxicillin has a very low (or even calculated "zero") average relative risk for sudden death. Further investigation into this outcome can be performed by applying filters, as shown in FIG. 9.

Figure 9:
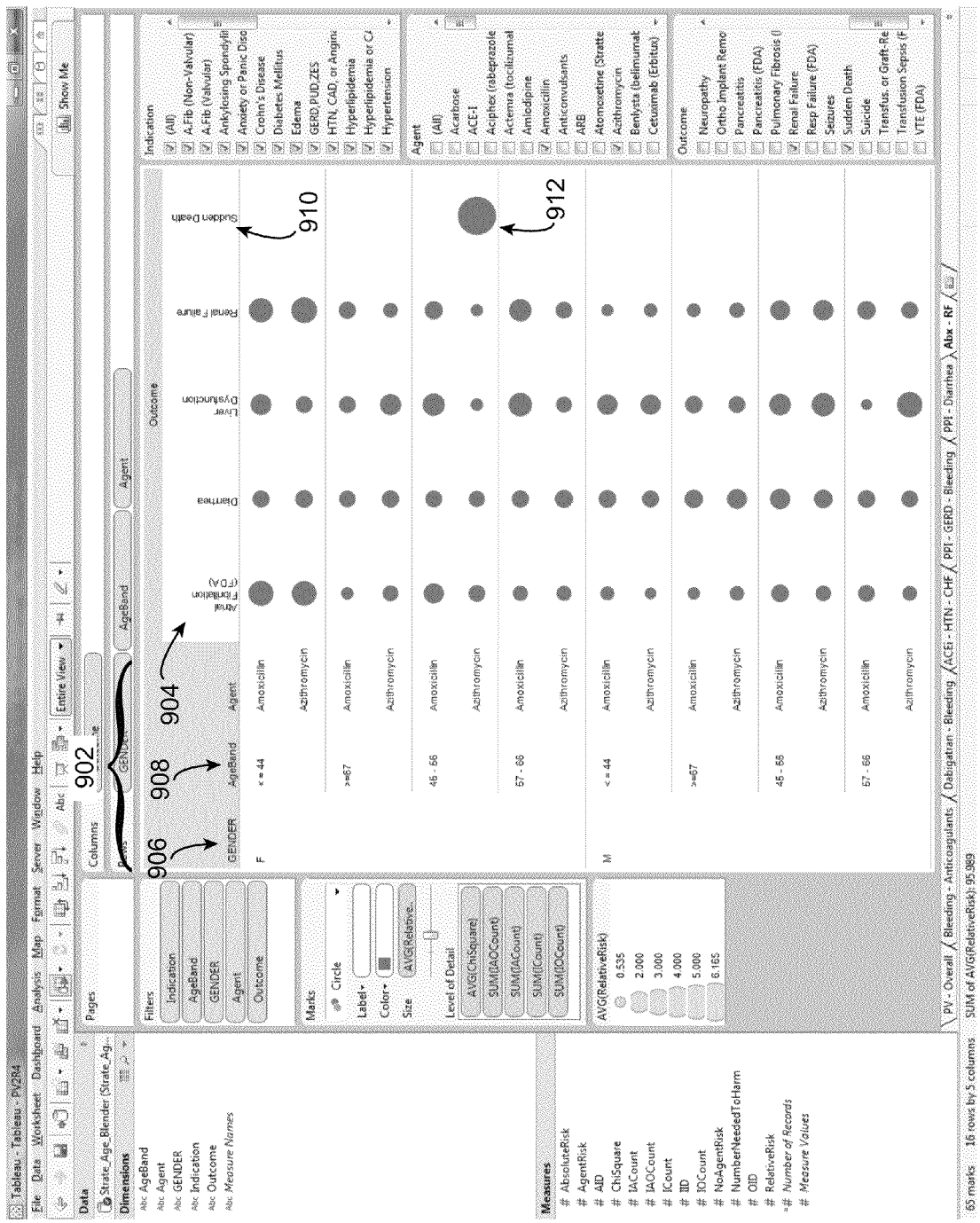
FIG. 9 is a screenshot of a user interface displaying an average relative risk for two agents relative to a plurality of outcomes, where the data is filtered by gender and age, in accordance with an embodiment of the disclosure.

FIG. 9 is a screenshot of a user interface displaying an average relative risk for two agents relative to a plurality of outcomes, where the data is filtered by gender and age, in accordance with an embodiment of the disclosure. In FIG. 9, five different outcomes are shown along the horizontal axis 904. Along the vertical axis 902, two different agents from the same class are shown. In this example, two different antibiotics are shown, amoxicillin and azithromycin. The agents are filtered first by gender 906 and then by age band 908. For the particular outcome in question, "Sudden Death" 910, filtering the data by gender and age band reveals that azithromycin has a relatively high average relative risk for sudden death for women ages 45-56. In one example, the analysis and calculation shown in FIG. 9 may, therefore, "exonerate" azithromycin from the risk of sudden death for all males and for females outside the ages of 45-56.

Figure 10:
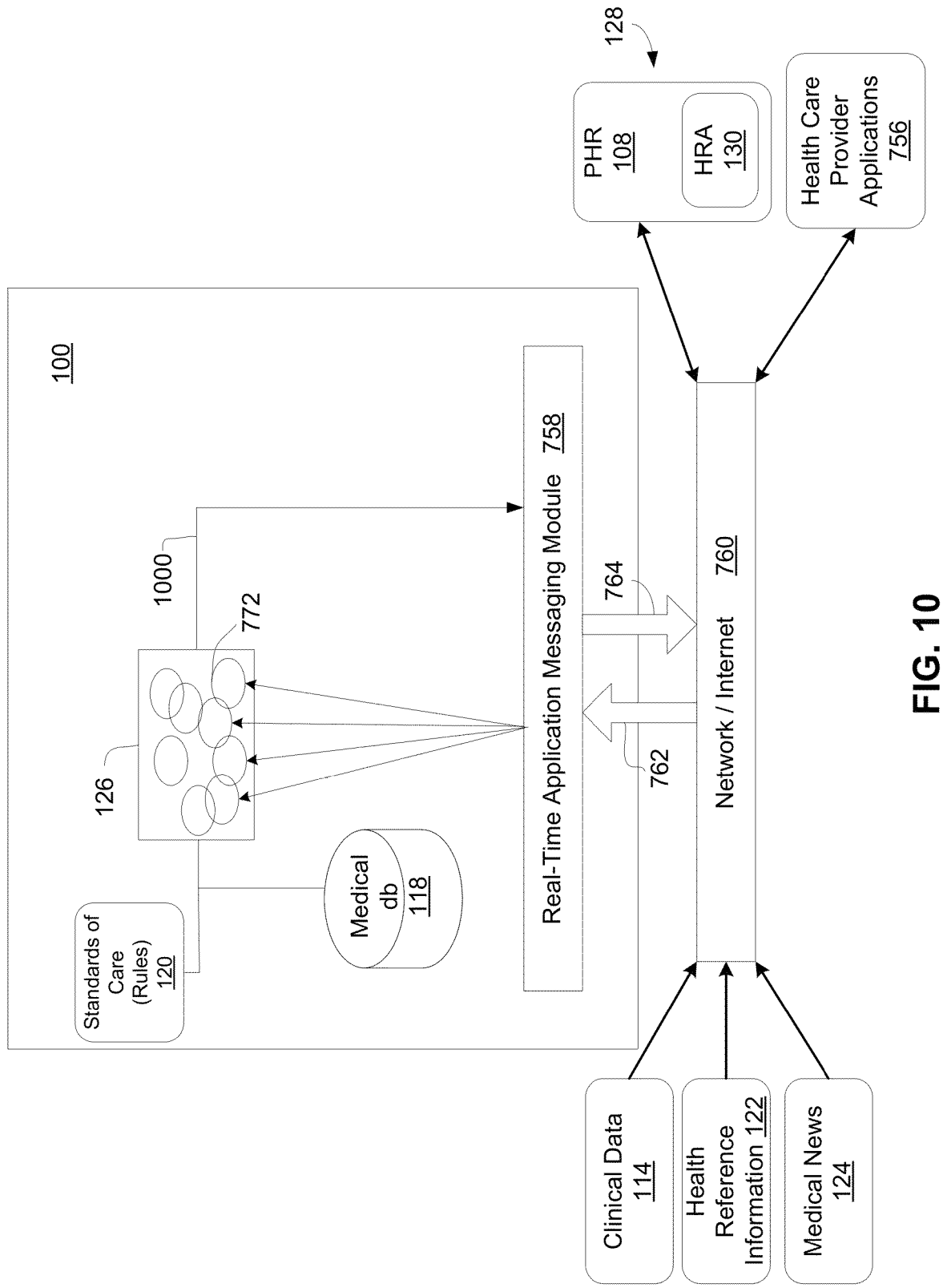
FIG. 10 is a schematic diagram illustrating an overview of a system for analyzing a relationship between one or more agents and one or more clinical outcomes, in accordance with an embodiment of the disclosure.

In the additional embodiment illustrated in FIG. 10, the system and method of the present disclosure implement a plurality of modules for providing real-time processing and delivery of calculated statistics about agents and outcomes. For example, the statistics may be presented to a health care provider 110 via one or more health care provider applications 756. In one implementation, health care organization 100 includes a real-time transfer module 758. The real-time transfer module 758 comprises computer executable instructions encoded on a computer-readable medium, such as a hard drive, of one or more server computers controlled by the health care organization 100. Specifically, the real-time transfer module 758 is configured to calculate statistics, such a risk scores, for real-time information received via a network 760 between the health care organization 100 and external systems and applications. Preferably, the real-time transfer module 758 employs a service-oriented architecture (SOA) by defining and implementing one or more application platform-independent software services to carry real-time data between various systems and applications.

In one embodiment, the real-time transfer module 758 comprises web services 762, 764 that interface with external applications for transporting the real-time data via a Simple Object Access Protocol (SOAP) over HTTP (Hypertext Transfer Protocol). The message ingest web service 762, for example, receives real-time data that is subsequently processed in real-time by the calculation engine 126. The message ingest web service 762 synchronously collects clinical data 114 from the medical insurance carrier 112, patient-entered data 128, including patient-entered clinical data 128, from the patient's PHR 108 and HRA 130, as well as health reference information 122 and medical news information 124. In an embodiment, the message ingest web service 762 also receives clinical data 114 in real-time from one or more health care provider applications 756, such as an electronic medical record (EMR) application and a disease management application. In yet another embodiment, the message ingest service 762 receives at least some of the patient-entered data 128 pursuant to the patient's interaction with a nurse in disease management or an integrated voice response (IVR) system. Incoming real-time data is optionally stored in the medical database 118. Furthermore, incoming real-time data associated with a given patient 102, in conjunction with previously stored data at the database 118 and the clinical rules 120, defines a rules engine run to be processed by the calculation engine 126. Hence, the real-time transfer module 758 collects incoming real-time data from multiple sources and defines a plurality of rules engine runs associated with one or more agents (e.g., drugs) and one or more outcomes (e.g., adverse events) for real-time processing.

The real-time transfer module 758 forwards the rules engine runs to the calculation engine 126 to instantiate a plurality of real-time rule processing sessions 772. The processing of the rule processing sessions 772 by the calculation engine 126 can be load-balanced across multiple logical and physical servers to facilitate multiple and simultaneous requests for real-time calculation of risk scores for one or more pairs of agents and outcomes. In one embodiment, the load-balancing of sessions 772 is accomplished in accordance with a J2EE (Java) specification. Each rule processing session 772 makes calls to the medical database 118 by referring to a unique agent ID field for a corresponding agent (e.g., drug) to receive data related to that agent for processing of incoming real-time data. The results 1000 of the real-time processing of the calculation engine may then be output to the real-time transfer module 758 for distribution to one or more health care provider applications 756 and/or to other servers and/or services via message output service 764.

In sum, embodiments described herein provide a system and method for pharmacovigilance, i.e., drug surveillance. The systems and methods described herein may, in some implementations, be used by drug companies or others (such as, for example, the FDA) to monitor and test the safety and efficacy of drugs with respect to certain outcomes. The systems and methods could be customized by applying certain filters to analyze the data at finer granularity.

Some embodiments compute the clinical context of a health outcome or adverse event, rather than simply pairing a drug to a health outcome of interest. In various implementations, this includes analyzing the existence of an FDA-labeled indication for the drug (i.e., on-label use versus off-label use), the relative frequency of the symptoms for the outcome of interest (e.g., dizziness or palpitations may be symptoms of an arrhythmia), the relative frequency of testing for the outcome of interest (e.g., Holter EKG monitoring may be used to detect arrhythmias) to calibrate whether frequency of the outcome of interest (e.g., there may appear to be more liver abnormalities just because more liver function testing was being done), the relative frequency of the outcome itself, and the relative frequency of "rescue treatments" related to the outcome, e.g. for a drug that causes diarrhea, the frequency of anti-diarrheal treatments (as opposed to episodes of the diarrhea itself).

Embodiments aggregate this data in a manner not only to detect new signals of drug-adverse event relationships, but can be configured in a way to "exonerate" or provide data to suggest that no agent-outcome relationship was detected, even though the sample size suggests a high probability that the relationship. In this way, drugs that may appear to be generating signals in the FDA AERS (Adverse Event Reporting System) may be compared against the signal confirmation versus exoneration findings calculated using embodiments of the disclosure. For example, using the embodiments disclosed herein, which are capable of updating on a near-real-time basis by running analysis on a frequent repeated basis (e.g., weekly, monthly), signals are detected earlier and trend analysis for emerging and/or fading signals can be performed more quickly.

All references, including publications, patent applications and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method for analyzing a relationship between at least two agents and one or more clinical outcomes, the method comprising:
   receiving a selection of at least two agents;
   receiving a selection of one or more clinical outcomes;
   for each of the at least two agents, analyzing in real-time or near real-time, by a processor included in a computing device, clinical data stored in a database to determine a number of occurrences of each of the one or more clinical outcomes when the agent is administered;
   for each of the at least two agents, calculating in real-time or near real-time, by the processor, a risk score for each clinical outcome, wherein, for each combination of agent and clinical outcome, calculating the risk score includes measuring a statistical significance of a relationship between the agent and the clinical outcome based on a total number of patients in an entire population, a number of patients to whom the agent is administered, a number of occurrences of the clinical outcome when the agent is administered, and a total number of patients in the entire population that experienced the clinical outcome;
   outputting the risk scores to a graphical display device, wherein, for a first agent of the at least two agents, a first risk score indicates that the first agent is not the cause of a first clinical outcome for a first sub-population that is a subset of the entire population, and wherein, for a second agent of the at least two agents, a second risk score identifies a possible benefit of the second agent for a second sub-population that is a subset of the entire population;
   generating a first hypothesis by the processor that is based on the first risk score that indicates that the first agent is not the cause of the first clinical outcome for the first sub-population;
   generating a second hypothesis by the processor that is based on the second risk score that identifies the possible benefit of the second agent for the second sub-population; and
   generating and outputting a message corresponding to the first hypothesis or the second hypothesis generated by the processor.

2. The method of claim 1, further comprising:
   filtering the clinical data stored in the database based on one or more filters, such that the risk scores are calculated using data that satisfies the one or more filters.

3. The method of claim 2, wherein the one or more filters include age, gender, clinical stratification scores and identified conditions, and/or an indication of use of the agent.

4. The method of claim 1, wherein the at least two agents comprise prescription drugs.

5. The method of claim 1, wherein each of the at least two agents is associated with a common class of agents, such that the first agent exhibits a relatively lower risk score for one of the clinical outcomes compared to the other agents in the common class of agents.

6. The method of claim 1, wherein the clinical data stored in a database includes demographic data, lab data, pharmacy data, claims data, diagnostic codes, procedure codes, heath reference information, medical news, standards-of-care, and/or patient-entered data.

7. The method of claim 1, wherein outputting the risk scores comprises displaying, for each combination of agent and clinical outcome, a circle corresponding to the risk score, wherein a larger circles corresponds to a larger risk score.

8. The method of claim 1, further comprising, for each combination of agent and clinical outcome, calculating a confidence level for the risk scores based on the equation:

$$\frac{(I)[(IAO)(I-IO-IA+IAO)-(IO-IAO)(IA-IAO)]^2}{(IA)(I-IA)(IO)(I-IO)}$$

wherein:
   I represents the total number of patients in the entire population;
   IA represents the number of patients to whom the agent is administered;
   IAO represents the number of occurrences of the clinical outcome when the agent is administered; and
   IO represents the total number of patients in the entire population that experienced the clinical outcome.

9. A non-transitory computer-readable storage medium storing instructions that when executed by a processor cause a computer system to analyze a relationship between at least two agents and one or more clinical outcomes, by performing the steps of:
   receiving a selection of at least two agents;
   receiving a selection of one or more clinical outcomes;
   for each of the at least two agents, analyzing in real-time or near real-time clinical data stored in a database to determine a number of occurrences of each of the one or more clinical outcomes when the agent is administered;

for each of the at least two agents, calculating in real-time or near real-time a risk score for each clinical outcome, wherein, for each combination of agent and clinical outcome, calculating the risk score includes measuring a statistical significance of a relationship between the agent and the clinical outcome based on a total number of patients in an entire population, a number of patients to whom the agent is administered, a number of occurrences of the clinical outcome when the agent is administered, and a total number of patients in the entire population that experienced the clinical outcome; and outputting the risk scores to a graphical display device, wherein, for a first agent of the at least two agents, a first risk score indicates that the first agent is not the cause of a first clinical outcome for a first sub-population that is a subset of the entire population, and wherein, for a second agent of the at least two agents, a second risk score identifies a possible benefit of the second agent for a second sub-population that is a subset of the entire population;

generating a first hypothesis is generated by the processor that is based on the first risk score that indicates that the first agent is not the cause of the first clinical outcome for the first sub-population; and generating a second hypothesis by the processor that is based on the second risk score that identifies the possible benefit of the second agent for the second sub-population.

10. The computer-readable storage medium of claim 9, further comprising:

filtering the clinical data stored in the database based on one or more filters, such that the risk scores are calculated using data that satisfies the one or more filters.

11. The computer-readable storage medium of claim 10, wherein the one or more filters include age, gender, clinical stratification scores and identified conditions, and/or an indication of use of the agent.

12. The computer-readable storage medium of claim 9, wherein the at least two agents comprise prescription drugs.

13. The computer-readable storage medium of claim 9, wherein each of the at least two agents is associated with a common class of agents, such that the first agent exhibits a relatively lower risk score for one of the clinical outcomes compared to the other agents in the common class of agents.

14. The computer-readable storage medium of claim 9, wherein the clinical data stored in a database includes demographic data, lab data, pharmacy data, claims data, diagnostic codes, procedure codes, heath reference information, medical news, standards-of-care, and/or patient-entered data.

15. The computer-readable storage medium of claim 9, wherein outputting the risk scores comprises displaying, for each combination of agent and clinical outcome, a circle corresponding to the risk score, wherein a larger circles corresponds to a larger risk score.

16. The computer-readable storage medium of claim 9, further comprising, for each combination of agent and clinical outcome, calculating a confidence level for the risk scores based on the equation:

$$\frac{(I)[(IAO)(I-IO-IA+IAO)-(IO-IAO)(IA-IAO)]^2}{(IA)(I-IA)(IO)(I-IO)}$$

wherein:
I represents the total number of patients in the entire population;
IA represents the number of patients to whom the agent is administered;
IAO represents the number of occurrences of the clinical outcome when the agent is administered; and
IO represents the total number of patients in the entire population that experienced the clinical outcome.

17. A system comprising:
a clinical data database; and
a healthcare organization computing device executing one or more processors to analyze a relationship between at least two prescription drugs and one or more clinical outcomes, by performing the steps of:
receiving a selection of at least two prescription drugs,
receiving a selection of one or more clinical outcomes,
for each of the at least two prescription drugs, analyzing in real-time or near real-time clinical data stored in a database to determine a number of occurrences of each of the one or more clinical outcomes when the prescription drug is administered,
for each of the at least two prescription drugs, calculating in real-time or near real-time a risk score for each clinical outcome, wherein, for each combination of prescription drug and clinical outcome, calculating the risk score includes measuring a statistical significance of a relationship between the prescription drug and the clinical outcome based on a total number of patients in an entire population, a number of patients to whom the prescription drug is administered, a number of occurrences of the clinical outcome when the prescription drug is administered, and a total number of patients in the entire population that experienced the clinical outcome,
outputting the risk scores to a graphical display device, wherein, for a first prescription drug of the at least two prescription drugs, a first risk score indicates that the first prescription drug is not the cause of a first clinical outcome for a first sub-population that is a subset of the entire population, and wherein, for a second prescription drug of the at least two prescription drugs, a second risk score identifies a possible benefit of the second prescription drug for a second sub-population that is a subset of the entire population,
generating a first hypothesis that is based on the first risk score that indicates that the first prescription drug is not the cause of the first clinical outcome for the first sub-population, and
generating a second hypothesis that is based on the second risk score that identifies the possible benefit of the second prescription drug for the second sub-population.

18. The system of claim 17, wherein the one or more processors are further configured to:
filter the clinical data stored in the database based on one or more filters, such that the risk scores are calculated using data that satisfies the one or more filters.

19. The system of claim 18, wherein the one or more filters include age, gender, clinical stratification scores and identified conditions, and/or an indication of use of the prescription drug.

20. The system of claim 17, wherein each of the at least two prescription drugs is associated with a common class of prescription drugs, such that the first prescription drug exhibits a relatively lower risk score for one of the clinical outcomes compared to the other prescription drugs in the common class of prescription drugs.

21. The system of claim 17, wherein the clinical data stored in a database includes demographic data, lab data, pharmacy data, claims data, diagnostic codes, procedure codes, heath reference information, medical news, standards-of-care, and/or patient-entered data.

22. The system of claim 17, wherein outputting the risk scores comprises displaying, for each combination of prescription drug and clinical outcome, a circle corresponding to the risk score, wherein a larger circles corresponds to a larger risk score.

* * * * *